United States Patent [19]

Alig et al.

[11] Patent Number: 4,652,679

[45] Date of Patent: Mar. 24, 1987

[54] AZIRIDINE AND PHENETHANOLAMINE DERIVATIVES HAVING ANTIOBESITY AND ANTI-HYPERGLYCAEMIC ACITIVITY

[75] Inventors: Leo Alig, Kaiseraugst; Marcel Müller, Frenkendorf, both of Switzerland

[73] Assignee: Hoffmann-La Roche Inc., Nutley, N.J.

[21] Appl. No.: 492,981

[22] Filed: May 9, 1983

[30] Foreign Application Priority Data

May 14, 1982 [CH] Switzerland .......................... 3013/82
Mar. 16, 1983 [CH] Switzerland .......................... 1434/83

[51] Int. Cl.$^4$ .................. C07D 333/38; A61K 31/38; A61K 31/045; C07C 91/06
[52] U.S. Cl. ...................................... 564/86; 564/363; 564/365; 544/59; 544/60; 544/159; 544/160; 544/162; 544/163; 544/146; 544/374; 544/383; 544/399; 544/401; 546/213; 546/232; 546/233; 546/235; 549/61; 549/65; 549/72; 549/75; 549/76; 549/77; 548/954; 548/962; 548/967; 548/768
[58] Field of Search .................. 544/59, 160, 383, 162, 544/163, 159, 399, 401, 146, 60, 374; 564/363, 365, 86; 546/232, 233, 235, 213; 549/61, 65, 72, 75, 76, 77

[56] References Cited

U.S. PATENT DOCUMENTS

| | | | |
|---|---|---|---|
| 3,092,636 | 6/1963 | Heinzelman et al. | 548/569 |
| 3,514,465 | 5/1970 | Posselt et al. | 549/75 X |
| 3,621,052 | 11/1971 | Thiele | 564/285 X |
| 3,642,896 | 2/1972 | Collin | 564/358 |
| 3,644,353 | 2/1972 | Lunts et al. | 544/162 |
| 3,646,145 | 2/1972 | Thiele et al. | 564/342 |
| 3,658,845 | 4/1972 | Posselt et al. | 549/57 |
| 3,705,233 | 12/1972 | Lunts et al. | 424/45 |
| 3,715,369 | 2/1973 | Posselt et al. | 549/72 |
| 3,732,300 | 5/1973 | Lunts et al. | 564/165 |
| 3,803,173 | 4/1974 | Posselt | 549/58 X |
| 3,867,455 | 2/1975 | Atkinson et al. | 564/356 |
| 4,024,156 | 5/1977 | Bagli et al. | 549/70 X |
| 4,140,713 | 2/1979 | Oxford et al. | 564/86 |
| 4,374,149 | 2/1983 | Philion | 564/363 X |
| 4,379,166 | 4/1983 | Neustadt et al. | 564/363 X |
| 4,382,958 | 5/1983 | Duckworth | 514/653 |
| 4,419,363 | 12/1983 | Smith | 424/250 |
| 4,585,796 | 4/1986 | Alig et al. | 546/226 X |

FOREIGN PATENT DOCUMENTS

| | | |
|---|---|---|
| 6735 | 1/1980 | European Pat. Off. . |
| 7204 | 1/1980 | European Pat. Off. . |
| 7205 | 1/1980 | European Pat. Off. . |
| 7206 | 1/1980 | European Pat. Off. . |
| 6766 | 1/1980 | European Pat. Off. . |
| 21636 | 1/1981 | European Pat. Off. . |
| 23385 | 2/1981 | European Pat. Off. . |
| 25331 | 3/1981 | European Pat. Off. . |
| 29320 | 5/1981 | European Pat. Off. . |
| 28105 | 5/1981 | European Pat. Off. . |
| 40000 | 11/1981 | European Pat. Off. . |
| 40915 | 12/1981 | European Pat. Off. . |
| 50885 | 5/1982 | European Pat. Off. . |
| 68699 | 1/1983 | European Pat. Off. ............ 544/162 |
| 91749 | 10/1983 | European Pat. Off. .............. 564/86 |
| 95827 | 12/1983 | European Pat. Off. ............ 564/363 |
| 2145894 | 3/1972 | Fed. Rep. of Germany . |
| 108532 | 9/1974 | Fed. Rep. of Germany . |
| 2843016 | 4/1979 | Fed. Rep. of Germany . |
| 45721 | 2/1966 | German Democratic Rep. . |
| 2084577 | 4/1982 | United Kingdom . |

OTHER PUBLICATIONS

Chem. Ber. 107, 5-12 (1974).
Derwent 52543V (U.K. Pat. Spec. 1360-457, 1974).
Derwent 21199 (Belgian Pat. Spec. 666,985, 1965).
Derwent 54964E (OD, 153682, 1982).
Derwent 27588d (EP, 26298,1981).
Derwent 46378E (EP, 52963, 1982).
Derwent 32396 (NE., 67-16085, 1968).
Derwent 11381 (Fr., 1353729,1964).
Derwent 17691 (Bel., 655,285, 1965).
Derwent 9639C (E.P. Pat. Spec., 7716, 1980).
Derwent 4337 (Bel. Pat. Spec., 572,661, 1957).
Derwent 4362 (Bel. Pat. Spec., 612,995, 1961).
Derwent 31483 (Bel. 703,687, 1968).
Derwent G 9045 (SA. 66/6722, 1967).
Derwent 3331E (EP., 49728, 1982).
Derwent 14848A (JA, 075921, 1978).
Merli et al., Index Chemicus, vol. 88 (5) (1983) Abst #337401.

*Primary Examiner*—Donald G. Daus
*Assistant Examiner*—William A. Teoli, Jr.
*Attorney, Agent, or Firm*—Jon S. Saxe; Bernard S. Leon; Matthew Boxer

[57] ABSTRACT

Aziridine and phenethanolamine derivatives of formulae I and II-1

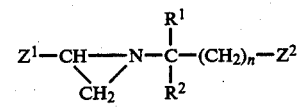

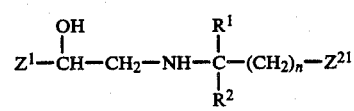

wherein $R^1$ and $R^2$ are hydrogen or lower-alkyl; $Z^1$ is phenyl or a phenyl group substituted in a defined manner; $Z^2$ and $Z^{21}$ are phenyl or thienyl substituted in a defined manner; and, n is an integer from 1-4. The disclosed compounds have catabolic activity and can be used for the treatment of obesity and/or of sugar illnesses. The compounds of formula I are obtained by dehydrating β-aminoalcohols (e.g. those of formula II-1) which, in turn, can be prepared by adding amines to epoxides or by reducing corresponding iminoketones, iminoalcohols a-keto-β-hydroxyamines or β-ketoamines.

13 Claims, No Drawings

AZIRIDINE AND PHENETHANOLAMINE DERIVATIVES HAVING ANTIOBESITY AND ANTI-HYPERGLYCAEMIC ACITIVITY

The present invention is concerned with novel aziridine derivatives, a process for their manufacture, novel intermediates therefor and pharmaceutical preparations based on the novel compounds.

The aziridine derivatives provided by the invention are compounds of the formula

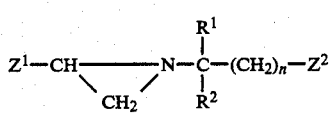
I wherein $Z^1$ is a group of the formula

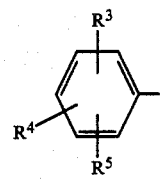

$Z^2$ is a group of the formula

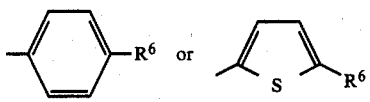

$R^1$ and $R^2$ are hydrogen or lower-alkyl;
$R^3$ is hydrogen, halogen, hydroxy, benzyloxy, lower-alkyl, lower-alkoxy, hydroxymethyl, amino, acylamino, lower-alkoxybenzylamino, nitro, carbamoyl, trifluoromethyl or lower-alkylsulphonylmethyl;
$R^4$ and $R^5$ are hydrogen, halogen or hydroxy;
$R^6$ is hydrogen, lower-alkyl, lower-alkanoyl, carboxy, cyano, hydroxy, hydroxy-lower-alkyl, acyloxy or a group $-C(R^7)=C(R^8)COOR^9$, $-SO_2R^{10}$, $-CH_2R^{10}$ or $-C(O)R^{10}$; $R^7$, $R^8$ and $R^9$ are hydrogen or lower-alkyl; $R^{10}$ is amino, mono- or di-lower-alkylamino, piperidino, morpholino, thiamorpholino, piperazino or the ether group of a lower aliphatic, cycloaliphatic or araliphatic alcohol or of a phenol; and n is a whole number of 1-4, and physiologically compatible salts thereof.

The term "lower" used herein denotes groups containing 1-6 carbon atoms, groups containing 1-4 carbon atoms being preferred. Alkyl and alkoxy groups can be straight-chain or branched-chain. Examples are methyl, ethyl, propyl, isopropyl, n-butyl and isobutyl or methoxy, ethoxy, propoxy, isopropoxy, butoxy and isobutoxy. Acyl groups are derived from aliphatic, araliphatic or aromatic carboxylic acids, for example lower-alkanecarboxylic acids such as formic acid, acetic acid, propionic acid and butyric acid; or phenyl-lower-alkanecarboxylic acids such as phenylacetic acid; or benzoic acid. Examples of alcohol groups $R^{10}$ are lower-alkoxy groups; cyclohexyloxy and cyclopentyloxy; as well as benzyloxy and substituted benzyloxy groups such as p-methoxybenzyloxy. Halogen is preferably chlorine or bromine.

The compounds of formula I form salts with acids and these salts are also an object of the present invention. Examples of such salts are salts with physiologically compatible mineral acids such as hydrochloric acid, hydrobromic acid, sulphuric acid and phosphoric acid; or with organic acids such as methanesulphonic acid, acetic acid, propionic acid, citric acid, succinic acid, malic acid, fumaric acid, phenylacetic acid or salicyclic acid. Carboxylic acids of formula I can also form salts. Examples of such salts are alkali metal, alkaline earth metal, ammonium and alkylammonium salts such as sodium, potassium, calcium, trimethylammonium and ethanolammonium salts.

The compounds of formula I contain one or more asymmetric carbon atoms and can therefore be present as optically active enantiomers, as diastereomers or as racemates.

The compounds of formula I and their salts can be manufactured in accordance with the invention by dehydrating a compound of the formula

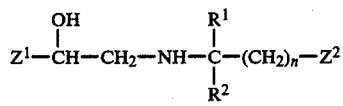
II wherein $Z^1$, $Z^2$, $R^1$, $R^2$ and n are as hereinbefore defined, and,
if desired, functionally modifying a reactive substituent present in the group $Z^2$ and/or converting the product into a physiologically compatible salt.

The dehydration of a compound of formula II can be carried out using triphenylphosphine/carbon tetrachloride as the dehydrating agent (Chem. Ber. 107, 1974, 5). This reaction is conveniently carried out in an inert organic solvent such as acetonitrile in the presence of a base (e.g. an amine such as triethylamine). The reaction temperature is not critical. The reaction is conveniently carried out at temperatures between room temperature and the boiling point of the reaction mixture, with room temperature or a slightly elevated temperature (e.g. 50° C.) being preferred.

The dehydration of a compound of formula II can also be carried out in two steps according to the methods of Gabriel or Wenker by replacing the hydroxy group by a halogen atom (e.g. by treatment with a halogenating agent such as thionyl chloride or phosphorus trichloride) or by converting the hydroxy group into a cleavable group (e.g. into a sulphuric acid ester) and treating the thus-obtained β-haloamine or β-amino hydrogen sulphate with alkali (e.g. alkali metal hydroxides such as sodium hydroxide).

As the functional modification of a substituent present in the group $Z^2$ of the compounds of formula I there come into consideration, for example, the esterification of a carboxy group, the saponification of an ester group, which can be present, for example, as the substituent $-C(O)R^{10}$, and the conversion of a carbamoyl group $R^6$ into a nitrile or aminomethyl group.

The esterification can be carried out in a manner known per se; for example, by means of alkyl halides such as methyl iodide and a base.

The saponification of an ester group is conveniently carried out under alkaline conditions, for example by means of aqueous-alcoholic alkali hydroxides (e.g. aqueous-methanolic potassium hydroxide).

A carbamoyl group $R^6$ can be dehydrated to the cyano group by means of triphenylphosphine/carbon tetrachloride in the presence of a base (e.g. an amine such as triethylamine) in a solvent such as acetonitrile.

A carbamoyl group $R^6$ can be reduced to the aminomethyl group, for example by means of lithium aluminum hydride in a solvent such as tetrahydrofuran.

Certain starting materials of formula II are known, for example from European Patent Applications 21636 A1 and 6735 A1.

The compounds of the formula

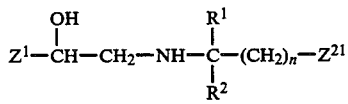   II-1 wherein
$Z^{21}$ is a group

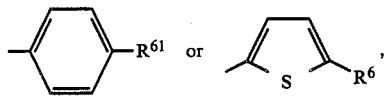

$R^{61}$ is a group $-CH_2R^{11}$ or $-SO_2R^{10}$;
$R^{11}$ is piperidino, morpholino, thiamorpholino or piperazino and
$Z^1$, $R^1$, $R^2$, $R^6$ and $R^{10}$ are as hereinbefore defined with respect to compounds of formula I,
and their physiologically compatible salts are novel and are also an object of the present invention. Furthermore, the present invention is concerned with pharmaceutical preparations based on the compounds of formula II-1 and with a process for the manufacture of these compounds.

The compounds of formula II-1 can be prepared by
(a) reacting a compound of the formula

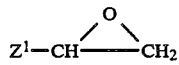   III with a compound of the formula

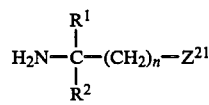   IV or
(b) reducing a compound of one of the formulae

   V

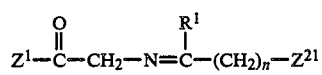   VI

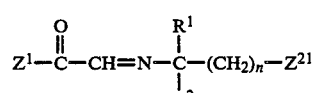   VII

-continued

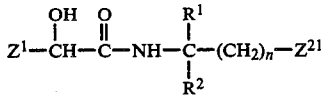   VIII

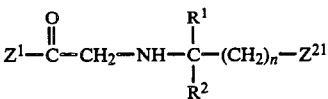   IX whereby in the foregoing formulae $Z^1$, $Z^{21}$, $R^1$, $R^2$ and n are as hereinbefore defined.

The reaction of a compound of formula III with a compound of formula IV can be carried out in an inert organic solvent, conveniently a protic solvent such as a lower alkanol (e.g. ethanol). The reaction temperature is not critical; it can lie between room temperature and the reflux temperature of the reaction mixture.

The reduction of a compound of formula V can be carried out by catalytic hydrogenation (e.g. in the presence of noble metal catalysts such as palladium or platinum catalysts) or by treatment with a complex metal hydride such as sodium borohydride. The reaction conditions used can be those which are usual for such reductions. The catalytic hyrogenation is conveniently carried out in inert organic solvent such as a lower alkanol (e.g. ethanol) at room temperature or at a slightly elevated temperature (e.g. at 20°–80° C.). The reaction with a complex metal hydride is conveniently carried out in a lower alkanol (e.g. methanol) at temperatures of 20°–30° C.

The compounds of formulae VI, VII, VIII and IX can be reduced with a complex metal hydride in an analogous manner to the reduction of compounds of formula V. Sodium borohydride is a suitable complex metal hydride for the reduction of the compounds of formulae VI and VII. The compounds of formula VIII are conveniently reduced with lithium aluminium hydride.

Preferred compounds of formulae I and II-1 are those in which $R^1$ is hydrogen and $R^2$ is hydrogen or methyl, especially methyl; and/or in which $R^3$ is hydrogen, lower-alkyl, lower-alkoxy, halogen or trifluoromethyl; $R^4$ is hydrogen or halogen and $R^5$ is hydrogen. Especially preferred are those compounds in which $R^3$ is hydrogen, chlorine or trifluoromethyl, especially in the meta-position, and $R^4$ and $R^5$ are hydrogen.

Preferred compounds of formula I are those in which $R^6$ is a group $-CH_2R^{10}$, $-C(O)R^{10}$ or $-SO_2R^{10}$, with a group $-C(O)R^{10}$, especially carbamoyl, being particularly preferred. Examples of such compounds are p-[(S)-3-[(S)-2-phenyl-1-aziridinyl]butyl]benzamide and physiologically compatible salts thereof.

Preferred compounds of formula II-1 are those in which $R^{61}$ is sulphamoyl or in which $R^6$ is a group $-CH_2R^{10}$, $-C(O)R^{10}$, $-SO_2R^{10}$ or $-C(R^7)=C(R^8)COOR^9$. Especially preferred are those compounds in which $R^6$ is a group $-C(O)R^{10}$ or $-C(R^7)=C(R^8)COOR^9$ in which $R^7$ and $R^9$ are lower-alkyl and $R^8$ is hydrogen, especially carbamoyl or 2-ethoxycarbonyl-1-methylvinyl.

The compounds of formula I and II-1 and their salts can be used as active substances in pharmaceutical preparations for the treatment of obesity and/or of diabetes mellitus, especially of obese adult diabetics. In an animal experiment an increased catabolism, primarily of fat, has been observed following the administration of compounds of formulae I and II-1. Furthermore, it has been observed that the compounds of formulae I and II-1 stimulate the formation of brown adipose tissue in rats and obese hyperglycaemic mice. It is known that defects of the brown adipose tissue play a substantial role in the origin of obesity. In obese hyperglycaemic mice the compounds of formulae I and II-1 have a pronounced antidiabetic effect, in that they have hypoglycaemic activity and reduce glucosuria. The compounds of formulae I and II-1 exhibit only a slight activity on the working of the heart and circulation. The dosage can amount to 0.5–1000 mg, preferably 2–200 mg, per day for an adult depending on the strength of activity of the individual compounds and on the individual requirements of the patients, whereby the dosage can be administered as a single dosage or in several dosages divided over the day.

The pharmaceutical preparations contain the active substance together with a compatible pharmaceutical organic or inorganic carrier material such as, for example, water, gelatine, gum arabic, lactose, starch, magnesium stearate, talc, vegetable oils, polyalkylene glycols or petroleum jelly. The pharmaceutical preparations are preferably administered orally, for example in the form of tablets, capsules, pills, powders, granulates, solutions, syrups, suspensions or elixirs. The administration can, however, also be carried out parenterally, for example in the form of sterile solutions, suspensions or emulsions. The pharmaceutical preparations can be sterilized and/or can contain ingredients such as preserving agents, stabilizers, wetting agents, emulsifiers, salts for varying the osmotic pressure and buffer substances.

The activity of the novel compounds of formulae I and II-1 is evident from the following test results:

1. Activity on oxygen consumption

Male albino rats weighing 160–180 g were placed in metabolic cages after fasting for 24 hours. The cages were ventilated with a constant 6 liters of room air/hour which was equilibrated at a dew point of 11° C. During an adaptation period of 4 hours, samples of the spent air were collected at 14 minute intervals and, after again equilibrating the moisture content of these samples, the oxygen content and carbon dioxide content were analysed. From this data the average $O_2$ consumption of all of the test animals during the adaptation period was computed. Thereafter, the animals, which were divided into groups of 6, received either placebo (5% gum arabic) or one of several test substances (suspended in 5% gum arabic) per os. After being so medicated, the animals were again placed in the metabolic cages and, during the ensuring 12 hours, the spent air was collected and analysed as described above. From this data the average amount of $O_2$ consumed by the test animals, expressed as a percentage of the average $O_2$ consumption for the adaptation period, was calculated for the three hour period immediately following medication and for the entire 12 hour test period. The calculations for $O_2$ consumption of animals which received a test substance were then corrected to reflect variations in $O_2$ consumption noted in the placebo group during the test period. The results of these tests are summarized in Table I.

TABLE

| Compound prepared in Example No. | Dosage μM/kg | $O_2$ consumption (% of average $O_2$ consumption of adaptation period) | |
|---|---|---|---|
| | | 1st–3rd hour | 1st–12th hour |
| 1 | 30 | 151 | 112 |

TABLE-continued

| Compound prepared in Example No. | Dosage μM/kg | $O_2$ consumption (% of average $O_2$ consumption of adaptation period) | |
|---|---|---|---|
| | | 1st–3rd hour | 1st–12th hour |
| 2 | 10 | 132 | 109 |
| 4 | 10 | 142 | 120 |
| 6 | 100 | 117 | 111 |
| 8 | 1 | 150 | 114 |
| 9 | 100 | 145 | 119 |
| 10 | 30 | 142 | 114 |
| 11 | 10 | 160 | 118 |
| 12 | 30 | 123 | 108 |
| 14 | 300 | 142 | 137 |
| 15 | 100 | 146 | 127 |
| 16 | 100 | 131 | 106 |
| 17 | 300 | 169 | 137 |
| 18 | 300 | 118 | 122 |
| 21 | 30 | 162 | 124 |
| 22 | 100 | 125 | 122 |
| 23 | 10 | 137 | 111 |
| 24 | 100 | 121 | 110 |
| 25 | 100 | 116 | 109 |
| 27 | 10 | 127 | 108 |
| 28 | 30 | 152 | 122 |
| 29 | 3 | 133 | 114 |
| 30 | 3 | 120 | 110 |
| 31 | 100 | 170 | 138 |
| 32 | 300 | 160 | 131 |
| 33 | 100 | 155 | 125 |
| 36 | 30 | 158 | 122 |
| 37 | 100 | 172 | 127 |
| 38 | 1 | 154 | 119 |
| 39 | 10 | 134 | 111 |

2. Catabolic activity on lipids

Groups of 4 male albino rats weighing 320–360 g were kept in metabolic cages without access to feed. Oxygen consumption and carbon dioxide production were measured during 12 hours. After 4 hours, the animals received placebo (5% gum arabic) or the test substance (suspended in gum arabic) per os. In Table II there is given the average decrease of the respiratory quotient ($CO_2/O_2$) during 8 hours after administration of the test substance in comparison to the last 3 hours before administration of the test substance. Variations appearing in the placebo group were taken into consideration in the calculation.

TABLE II

| Compound prepared in Example No. | Dosage μM/kg | Variation of the Respiratory quotient |
|---|---|---|
| 5 | 30 | −0.020 |

3. Activity on urine glucose and blood glucose and the formation of brown adipose tissue Female hyperglycaemic obese mice were adapted to an amount of feed of 3 g/day/animal. The test compound (suspended in 5% gum arabic) or placebo (5% gum arabic) was administered orally twice daily during 15 days. Urine was collected for 6 days a week and urine glucose was determined. Blood glucose and the weight of the interscapular brown adipose tissue were determined at the end of the test.

The test results are given in Table III as a percentage of the control value.

TABLE III

| Compound prepared in Example No. | Dosage μM/kg/ per day | Urine glucose | | Blood glucose | Brown adipose tissue |
|---|---|---|---|---|---|
| | | 1st week | 2nd week | | |
| 5 | 180 | 48 | 33 | 53 | 159 |

The following Examples illustrate the present invention:

EXAMPLE 1

A mixture of 1.70 g of rac-p-[3-($\beta$-hydroxyphenethyl)-amino]propyl]benzamide, 0.8 ml of triethylamine, 0.6 ml of carbon tetrachloride, 1.65 g of triphenylphosphine and 12 ml of acetonitrile was warmed to 50° for 2.5 hours while stirring. For the working-up, the mixture was poured into ice-water, extracted with methylene chloride, the methylene chloride extract was washed with water, dried with sodium sulphate and evaporated in vacuo. The residue was chromatographed on 150 g of silica gel, using a mixture of chloroform, n-propanol and 25% aqueous ammonia (800:40:2). There was isolated 1.0 g of pure p-[3-(2-phenyl-1-aziridinyl)propyl]benzamide of melting point 89°–90° (recrystallised from methylene chloride/ether). UV: $\epsilon_{227}=14860$; $\epsilon_{236}=14300$.

EXAMPLE 2

In accordance with Example I, from p-[3-[[(R)-$\beta$-hydroxyphenethyl]amino]propyl]benzamide there was obtained p-[3-[(S)-2-propyl-1-aziridinyl]propyl]benzamide of melting point 101°–106°. $[\alpha]_D^{28}=+89°$ (c=0.5% in methanol); UV: $\epsilon_{224}=15900$.

EXAMPLE 3

In accordance with Example 1, from p-[3-[[(S)-$\beta$-hydroxyphenethyl]amino]propyl]benzamide there was obtained p-[3-[(R)-2-phenyl-1-ariridinyl]propyl]benzamide of melting point 106°–108° $[\alpha]_D^{20}=-95.5°$ (c=1.0% in methanol; UV: $\epsilon_{222}=16000$; $\epsilon_{236}=14700$.

EXAMPLE 4

In accordance with Example 1, from p-[(S)-3-[[(R)-$\beta$-hydroxyphenethyl]amino]butyl]benzamide there was obtained p-[(S)-3-[(S)-2-phenyl-1-aziridinyl]butyl]benzamide of melting point 129°–130° $[\alpha]_D^{20}=+125.5°$ (c=1.0% in methanol); UV: $\epsilon_{222}=15570$; $\epsilon_{236}=14150$ (shoulder).

EXAMPLE 5

A solution of 0.87 g of hydrogen chloride in 20 ml of ethyl acetate was added dropwise at 5°, while stirring, to a solution of 3.1 g of p-[(S)-3-[(S)-2-phenyl-1-aziridinyl]butyl]benzamide in 150 ml of ethyl acetate. The precipitate was filtered off under suction and recrystallized from methanol/ether. There was obtained pure p-[(S)-3-[(S)-2-phenyl-1-aziridinyl]butyl]benzamide dihydrochloride of melting point 186°–188°.

EXAMPLE 6

In accordance with Example 1, from p-[(S)-3-[[(S)-$\beta$-hydroxyphenethyl]amino]butyl]benzamide there was obtained p-[(S)-3-[(R)-2-phenyl-1-aziridinyl]butyl]benzamide of melting point 145°–146°. $[\alpha]_D^{20}=-64°$ (c=0.5% in methanol); UV: $\epsilon_{226}=16220$.

EXAMPLE 7

In accordance with Example 1, from p-[(S)-3-[[(R)-$\beta$-hydroxyphenethyl]amino]butyl]phenol there was obtained p-[(S)-3-[(S)-2-phenyl-1-aziridinyl]butyl]phenol of melting point 135°–136° (from ether). $[\alpha]_D^{20}=+131°$ (c=0.6% in methanol); UV: $\epsilon_{220}=14880$.

EXAMPLE 8

In accordance with Example 1, from p-[(R)-3-[[(R)-$\beta$-hydroxyphenethyl]amino]butyl]benzamide there was obtained p-[(R)-3-[(S)-2-phenyl-1-aziridinyl]butyl]benzamide of melting point 145°–146° (from acetone/hexane). $[\alpha]_D^{20}=+65°$ (c=1.0% in methanol); UV: $\epsilon_{226}=16540$.

EXAMPLE 9

In accordance with Example 1, from p-[3-[($\beta$-hydroxy-m-methoxyphenethyl)amino]propyl]benzamide there was obtained p-[3-[2-(m-methoxyphenyl)-1-aziridinyl]propyl]benzamide of melting point 130°–132° (from acetone/hexane) UV: $\epsilon_{226}=18750$; $\epsilon_{274}=2800$; $\epsilon_{280}=2240$.

EXAMPLE 10

1.73 g of triphenylphosphine, 1.83 g of (R,S)-5-[3-[($\beta$-hydroxyphenethyl)amino]propyl]-2-thiophenecarboxamide, 0.84 ml of triethylamine, 0.58 ml of carbon tetrachloride and 12 ml of acetonitrile were stirred at 25° for 18 hours. The mixture was evaporated in vacuo. The residue was dissolved in methylene chloride and extracted three times with ice-cold 2N hydrochloric acid. The acidic solutions were made basic with sodium hydroxide solution and extracted three times with methylene chloride. The methylene chloride solutions were washed neutral with water, dried and evaporated in vacuo. Chromatography of the residue on silica gel with ether/acetone (9:1) gave 800 mg of (R,S)-5-[3-(2-phenyl-1-aziridinyl)propyl]-2-thiophenecarboxamide of melting point 117°–119° (from acetonitrile). UV: $\epsilon_{217}=12290$; $\epsilon_{256}=8470$; $\epsilon_{275}=10620$.

EXAMPLE 11

In accordance with Example 10, from (R)-5-[3-[($\beta$-hydroxyphenethyl)amino]propyl]-2-thiophenecarboxamide there was obtained (S)-5-[3-(2-phenyl-1-aziridinyl)propyl]-2-thiophenecarboxamide of melting point 95°–98° $[\alpha]_D^{20}=+96°$ (c=1.0% in methanol); UV: $\epsilon_{218}=12100$; $\epsilon_{256}=8830$; $\epsilon_{275}=11200$.

EXAMPLE 12

A mixture of 2.98 g of p-[3-[[(R)-$\beta$-hydroxyphenethyl]amino]propyl]benzamide, 3.0 ml of triethylamine, 2.2 ml of carbon tetrachloride, 5.5 g of triphenylphosphine and 100 ml of acetonitrile was heated to reflux for 1 hour. For the working-up, the mixture was poured into ice-water and extracted with ethyl acetate. The ethyl acetate extract was washed with water, dried with sodium sulphate and evaporated in vacuo. The residue was chromatographed on 400 g of silica gel, using hexane/acetone (9:1), and there was eluted pure p-[3-[(S)-2-phenyl-1-aziridinyl]propyl]phenyl cyanide as a colourless oil. $[\alpha]_D^{20}=+92.4°$ (c=1.0% in methanol); UV: $\epsilon_{231}=19600$.

EXAMPLE 13

In accordance with Example 1, from p-[(S)-3-[[(R)-$\beta$-hydroxyphenethyl]amino]butyl]benzamide there was obtained p-[(S)-3-[(S)-2-phenyl-1-aziridinyl]butyl]benzamide.

EXAMPLE 14

In accordance with Example 1, from p-[3-[($\beta$-hydroxy-m-trifluoromethyl-phenethyl)amino]propyl]benzamide there was obtained p-[3-[2-(m-trifluoromethylphenyl)-1-aziridinyl]propyl]benzamide of melting point 135°-138° (from acetone/hexane).

EXAMPLE 15

In accordance with Example 1, from p-[3-[(β-hydroxy-m-chlorophenethyl)amino]propyl]benzamide there was obtained p-[3-[2-(m-chlorophenyl)-1-aziridinyl]propyl]benzamide of melting point 124°-125° (from acetone/hexane).

EXAMPLE 16

In accordance with Example 1, from methyl rac-p-[3-[(β-hydroxyphenethyl)amino]propyl]benzoate there was obtained methyl p-[3-(2-phenyl-1-aziridinyl)-propyl]benzoate. Oil; UV: $\epsilon_{214}=11040$; $\epsilon_{239}=17330$; $\epsilon_{270}=1230$.

EXAMPLE 17

In accordance with Example 1, from p-[(R)-3-[[(S)-β-hydroxyphenethyl]amino]butyl]benzamide there was obtained p-[(R)-3-[(R)-2-phenyl-1-aziridinyl]butyl]benzamide of melting point 122°-123° (from acetone/hexane). UV: $\epsilon_{222}=15630$; $\epsilon_{236}=14400$.

EXAMPLE 18

In accordance with Example 1, from p-[3-[(β-hydroxy-3,5-dichlorophenethyl)amino]propyl]benzamide there was obtained p-[3-[2-(3',5'-dichlorophenyl)-1-aziridinyl]propyl]benzamide of melting point 155°-156° (from acetone/hexane).

EXAMPLE 19

In accordance with Example 1, from methyl p-[(S)-2-[(R,S)-β-hydroxy-m-(trifluoromethyl)phenethyl-]amino]propyl]-β-methylcinnamate there were obtained methyl β-methyl-p-[(S)-2-[(R)-2-(α,α,α-trifluoro-m-tolyl)-1-aziridinyl]propyl]cinnamate as a yellow oil, $[\alpha]_D^{20}=-27°$ (c=0.3% in methanol), $\epsilon_{274}=20600$, and methyl β-methyl-p-[(S)-2-[(S)-2-(α,α,α-trifluoro-m-tolyl)-1-aziridinyl]propyl]cinnamate as a yellow oil, $[\alpha]_D^{20}=+161°$ (c=0.5% in methanol); UV: $\epsilon_{275}=19100$.

EXAMPLE 20

In accordance with Example 1, from methyl p-[(R)-2-[[(R,S,)-β-hydroxy-m-(trifluoromethyl)phenethyl-]amino]propyl]-β-methylcinnamate there were obtained methyl β-methyl-p-[(R)-2-[(S)-2-[α,α,α-trifluoro-m-tolyl)-1-aziridinyl]propyl]cinnamate as a yellow oil, $[\alpha]_D^{20}=+26.4°$ (c=0.5% in methanol), $\epsilon_{274}=20700$, and methyl β-methyl-p-[(R)-2-[(R)-2-(α,α,α-trifluoro-m-tolyl-1-aziridinyl]propyl]cinnamate as a yellow oil, $[\alpha]_D^{20}=-161.6°$ (c=0.6% in methanol); UV: $\epsilon_{274}=18950$.

EXAMPLE 21

In accordance with Example 1, from p-[(R,S)-3-[[(R)-β-hydroxy-phenethyl]amino]butyl]-N,N-dimethylbenzamide there was obtained p-[(R,S)-3-[(S)-2-phenyl-1-aziridinyl]butyl]-N,N-dimethylbenzamide; amorphous; UV: $\epsilon_{218}=18700$ (1:3 diastereomer mixture).

EXAMPLE 22

A mixture of 2.8 g of p-[3-[(S)-2-phenyl-1-aziridinyl]propyl]benzamide and 1.5 g of lithium aluminium hydride in 400 ml of absolute tetrahydrofuran was stirred at room temperature for 6 hours. The mixture was then treated dropwise with 3 ml of saturated sodium sulphate solution and subsequently the white precipitate was filtered off and rinsed with methylene chloride. The filtrate was evaporated in vacuo and the residue was chromatographed on 200 g of silica gel, using chloroform/n-propanol/saturated ammonia solution (800:50:3). There was eluted 1.95 g of pure p-[3-[(S)-2-phenyl-1-aziridinyl]propyl]benzylamine as a colourless liquid.

EXAMPLE 23

In accordance with Example 1, from p-[(S)-2-[[(R)-β-hydroxyphenethyl]amino]butyl]N]methylbenzamide there was obtained p-[(S)-3[(S)-2-phenyl-1-aziridinyl]-butyl]-N-methylbenzamide of melting point 113°-114°. $[\alpha]_D^{20}=120.7°$ (c=0.4% in methanol).

EXAMPLE 24

In accordance with Example 1, from p-[3-[[(R)-β-hydroxyphenethyl]amino]propyl]toluene there was obtained p-[3[(S)-2-phenyl-1-aziridinyl]propyl]toluene as a colourless liquid. $[\alpha]_D^{20}=+101.5°$ (c=1.0% in methanol); UV: $\epsilon_{217}=16030$.

EXAMPLE 25

In accordance with Example 1, from p-[3-[[(R)-β-hydroxyphenethyl]amino]propyl]benzene there was obtained p-[3-[(S)-2-phenyl-1-aziridinyl]propyl]benzene as a colourless liquid. $[\alpha]_D^{20}=+100°$ (c=1.0% in methanol); UV: $\epsilon_{216}=12150$.

EXAMPLE 26

In accordance with Example 1, from p-[3-[[(R)-β-hydroxyphenetyl]amino]propyl]benzenesulphonamide there was obtained p-[3-[(S)-2-phenyl-1-aziridinyl]-propyl]benzenesulphonamide of melting point 161°-163°.

EXAMPLE 27

A mixture of 20.0 g of 3-(4-aminosulphonylphenyl)-propylamine, 16.8 g (R)-styrene oxide and 500 ml of acetonitrile was heated under reflux for 40 hours. The solvent was then evaporated in vacuo and the residue was chromatographed on 1 kg of silica gel, using with chloroform/n-propanol/25% ammonia (1600:100:4). There was isolated 8.3 g of pure p-[3-[[(R)-β-hydroxyphenethyl]amino]propyl]-benzenesulphonamide of melting point 165°-166° (from acetonitrile). $[\alpha]_D^{20}=-13.4°$ (c=1.0% in methanol); UV: $\epsilon_{224}=14710$.

The amine starting material was prepared as follows:

p-Aminosulphonylbenzaldehyde was reacted with diethyl cyanomethylphosphonate/sodium hydride in tetrahydrofuran to give 1-cyano-2-(4-aminosulphonylphenyl)-ethane which was hydrogenated in methanol with Raney-cobalt as the catalyst to give 3-(4-aminosulphonylphenyl)-propylamine.

EXAMPLE 28

In accordance with Example 27, from (R)-styrene oxide and (S)-1-methyl-3-(4-aminosulphonylphenyl)-propylamine there was obtained p-[(S)-3-[[(R)-β-hydroxyphenethyl]amino]butyl]benzenesulphonamide of melting point 134°-135° (from acetone/hexane), $[\alpha]_D^{20}=-27.5$ (c=0.2 in methanol); UV: $\epsilon_{263}=26420$.

The amine starting material was prepared as follows:

4-(4-Aminosulphonylphenyl)butanone-2 was reacted with (S)-(−)-α-phenylethylamine and p-toluenesulphonic acid as the catalyst in toluene with separation of water to give the Schiff's base (S)-N-(α-methylbenzyl)-1-methyl-3-(4-aminosulphonylphenyl)propylimine. The imine was hydrogenated in methanol in the presence of Raney-nickel to give a mixture of the optical isomers of N-(α-methylbenzyl)-1-methyl-3-(4-aminosulphonylphenyl)propylamine. The amine was converted with oxalic acid into a mixture of the oxalates from which there was obtained by two-fold crystallization pure (S)-1-methyl-3-(4-aminosulphonylphenyl)propylamine oxalate of melting point 123°–127°, $[\alpha]_D^{20} = -68°$ (c=1.0 in methanol). Hydrogenolysis of this substance in alcohol under 4 bar of hydrogen at 60° for 24 hours yielded pure (S)-1-methyl-3-(4-aminosulphonylphenyl)propylamine.

EXAMPLE 29

In accordance with Example 27, from (R)-styrene oxide and (R)-1-methyl-3-(4-aminosulphonylphenyl)propylamine there was obtained p-[(R)-3-[[[(R)-β-hydroxyphenethyl]amino]-3-methylpropyl]benzenesulphonamide of melting point 135°–138° (from acetone/hexane). $[\alpha]_D^{20} = 0°$ (c=0.5% in methanol); UV: $\epsilon_{225} = 14600$.

EXAMPLE 30

10 g of 5-(3-aminopropyl)-2-thiophenecarboxamide and 6.8 ml of (R,S)-phenylethylene oxide were heated to 95° in 136 ml of dimethyl sulphoxide for 18 hours. The mixture was diluted with water and methylene chloride and the aqueous phase was extracted twice with methylene chloride. The methylene chloride phases were washed with water, dried over sodium sulphate and evaporated in vacuo. Chromatography of the residue with methanol on silica gel gave 7.85 g of (R,S)-5-[3-[(β-hydroxyphenethyl)amino]propyl]-2-thiophenecarboxamide of melting point 116°–117° (from methanol/ether). UV: $\epsilon_{257} = 8830$, $\epsilon_{276} = 10990$.

EXAMPLE 31

In a manner analogous to that described in Example 30 from 5-(3-aminopropyl)-2-thiophenecarboxamide and (R)-phenylethylene oxide there was obtained (R)-5-[3-[(β-hydroxyphenethyl)amino]propyl]-2-thiophenecarboxylic acid amide of melting point 89°–93°. $[\alpha]_{589} = -19°$ (c=0.1% in dioxane); UV: $\epsilon_{256} = 8600$; $\epsilon_{276} = 10790$.

EXAMPLE 32

In a manner analogous to that described in Example 30, from 5-(3-aminopropyl)-2-thiophenecarboxamide and (S)-phenylethylene oxide there was obtained (S)-5-[3-[(β-hydroxyphenethyl)amino]propyl]-2-thiophenecarboxamide of melting point 94°–96°. $[\alpha]_{589} = +19°$ (c=0.1% in dioxane); UV: $\epsilon_{256} = 8490$; $\epsilon_{275} = 10780$.

The amide starting material can be prepared as follows:

2-(p-Toluenesulphonyloxy)propylthiophene (J. Org. Chem. 36, 1971, 2236) was reacted with acetyl chloride and aluminium trichloride in methylene chloride to give 5-acetyl-2-(p-toluenesulphonyloxy)propylthiophene. Therefrom there was obtained with sodium azide in dimethyl sulphoxide 5-(3-azidopropyl)-2-thienyl methyl ketone. Oxidation with hypobromide gave 5-(3-azidopropyl)-2-thiophenecarboxylic acid of melting point 71°–72°. Reaction of this acid with thionyl chloride and subsequent treatment with concentrated ammonia gave 5-(3-azidopropyl)-2-thiophenecarboxamide of melting point 85°–87°. Therefrom there was obtained, after treatment with triphenylphosphine and hydrolysis (J. Org. Chem. 40, 1975, 1659), 5-(3-aminopropyl)-2-thiophenecarboxamide of melting point 143.5°–144° (from water).

EXAMPLE 33

2.58 g of 5-[3-[[(R)-β-hydroxyphenethyl]amino]propyl]-2-thiophenecarboxamide were treated portionwise in 129 ml of tetrahydrofuran under argon with 1.29 g of lithium aluminium hydride and the mixture was boiled at reflux for 3.25 hours. Then, while cooling, there were cautiously added 34 ml of 2N sodium hydroxide solution and subsequently 400 ml of water and the mixture was extracted three times with chloroform. The chloroform solutions were washed neutral with water and dilute sodium chloride solution, dried and evaporated in vacuo. Chromatography on silica gel with methanol and 0.5% concentrated ammonia and crystallization from acetonitrile/ether gave 914 mg of (R)-α-[[[3-[5-(aminomethyl)-2-thienyl]propyl]amino]methyl]benzyl alcohol of melting point 64°–65°. $[\alpha]_D = -18°$ (c=0.1% in dioxane); UV: $\epsilon_{240} = 9080$.

EXAMPLE 34

In a manner analogous to that described in Example 33, from (R,S)-5-[3-[(β-hydroxyphenethyl)amino]propyl]-2-thiophenecarboxamide there was obtained (R,S)-α-[[[3-[5-(aminomethyl)-2-thienyl]propyl]amino]methyl]benzyl alcohol of melting point 89°–90°. UV: $\epsilon_{240} = 8320$.

EXAMPLE 35

9.91 g of (R,S)-5-(3-aminobutyl)-2-thiophenecarboxamide and 5.7 ml of (R)-phenylethylene oxide were heated to 100° for 47 hours in 100 ml of dimethyl sulphoxide. The mixture was poured into water and extracted three times with methylene chloride. The methylene chloride solutions were washed with water and dilute sodium chloride solution dried and evaporated in vacuo. Chromatography of the residue on silica gel with ether/methanol (4:1) gave 7.35 g of 5-[(R,S)-3-[[(R)-β-hydroxyphenethyl]amino]butyl]-2-thiophenecarboxamide of melting point 124°–125° (from acetonitrile). $[\alpha]_D = -24°$ (c=0.1% in dioxane). UV: $\epsilon_{256} = 8500$; $\epsilon_{275} = 10830$.

The amide starting material can be prepared as follows:

4-(5-Acetyl-2-thienyl)-2-butanone (Tetrahedron 35, 1979, 329) was reacted with ethylene glycol, triethyl orthoformate and p-toluenesulphonic acid in methylene chloride to give methyl 5-[2-(2-methyl-1,3-dioxolan-2-yl)ethyl]-2-thienyl ketone. Oxidation with sodium hypobromite and subsequent hydrolysis gave 5-(3-oxobutyl)-2-thiophene carboxylic acid. With sodium borohydride there was obtained therefrom 5-(3-hydroxybutyl)-2-thiophenecarboxylic acid which was converted in dimethylacetamide with methyl iodide and sodium carbonate into the methyl ester. Treatment with p-toluenesulphochloride in pyridine and reaction with sodium azide in dimethyl sulphoxide gave methyl 5-(3-azidobutyl)-2-thiophenecarboxylate from which there was obtained by saponification the corresponding acid. The acid was treated with thionyl chloride to give the acid chloride from which there was obtained with concentrated ammonia in ether 5-(3-azidobutyl)-2-thiophenecarboxamide. Reduction of the azido group with triphenylphosphine and subsequent hydrolysis gave (R,S)-5-(3-aminobutyl)-2-thiophenecarboxamide of melting point 65°–75°. UV: $\epsilon_{256}=7780$; $\epsilon_{275}=9900$.

EXAMPLE 36

The following compounds were prepared in a manner analogous to that described in Example 10:
(a) 5-[(R,S)-3-[(S)-2-phenyl-1-aziridinyl]butyl]-2-thiophenecarboxamide of melting point 76°–78°; $[\alpha]_D^{20}=+99°$; (c=0.1% in dioxane); UV: $\epsilon_{275}=10560$;
(b) p-[2-[(S)-2-phenyl-1-aziridinyl]ethyl]benzamide of melting point 121°–122°; $[\alpha]_D^{20}=+113°$ (c=0.1% in methanol); UV: $\epsilon_{225}=15930$;
(c) methyl 5-[3-(S)-(2-phenyl-1-aziridinyl)propyl]-2-thiophenecarboxylate, $[\alpha]_D^{20}=+95°$ (c=0.1% in dioxane); UV: $\epsilon_{278}=12420$, $\epsilon_{254}=9360$.

The methyl 5-(3-aminopropyl)-2-thiophenecarboxylate used for the preparation of the aziridine in section (c) can be prepared by esterifying 5-(3-azidopropyl)-2-thiophenecarboxylic acid with methyl iodide and catalytically hydrogenating the thus-obtained methyl 5-(3-azidopropyl)-2-thiophenecarboxylate.

EXAMPLE 37

The following compounds were prepared in a manner analogous to that described in Example 30:
(a) Methyl 5-[3-[[(R)-β-hydroxyphenethyl]amino]propyl]-2-thiophenecarboxylate of melting point 81°–82°; $[\alpha]_D^{20}=-15°$ (c=0.1% in dioxane); UV: $\epsilon_{254}=9340$, $\epsilon_{277}=12410$;
(b) ethyl (E)-5-[(R,S)-3-[[(R)-β-hydroxyphenethyl]amino]butyl]-β-methyl-2-thiopheneacrylate of melting point 72°; $[\alpha]_D^{20}=-19°$ (c=0.1% in dioxane); UV; $\epsilon_{326}=18690$;
(c) 5-[2-[[(R)-β-hydroxyphenethyl]amino]ethyl]-2-thiophenecarboxamide of melting point 95°–97°; $[\alpha]_D^{20}=-27°$ (c=0.1% in methanol); UV: $\epsilon_{257}=9000$; $\epsilon_{275}=10520$;
(d) 5-[(R,S)-2-[[(R)-β-hydroxyphenethyl]amino]propyl]-2-thiophenecarboxamide; $[\alpha]_D^{20}=-18°$ (c=0.1% in dioxane); UV: $\epsilon_{257}=8560$; $\epsilon_{275}'10340$;
(e) ethyl (E)-5-[(R,S)-3-[[(R,S)-β-hydroxy-m-(trifluoromethyl)phenethyl]amino]butyl]-β-methyl-2-thiopheneacrylate, UV: $\epsilon_{321}=16730$;
(f) 5-[(R,S)-3-[[(R,S)-β-hydroxy-m-(trifluoromethyl)phenethyl]amino]butyl]-2-thiophenecarboxamide of melting point 165°–166°; UV: $\epsilon_{275}=11000$;
(g) ethyl (E)-5-[(R,S)-2-[[(R)-β-hydroxyphenethyl]amino]propyl]-β-methyl-2-thiophenecarboxylate; $[\alpha]_D^{20}=-14°$ (c=0.1% in dioxane); UV: $\epsilon_{320}=17130$;
(h) ethyl (E)-5-[(R,S)-2-[[(R,S)-β-hydroxy-m-(trifluoromethyl)phenethyl]amino]propyl]-β-methyl-2-thiopheneacrylate of melting point 101°–102°; UV: $\epsilon_{321}=19140$;
(i) 5-[(R,S)-3-[[(R)-β-hydroxyphenethyl]amino]butyl]-2-thienyl methyl ketone of melting point 66°–68°; $[\alpha]_D^{20}=-19°$ (c=0.1% in dioxane); UV: $\epsilon_{264}=8730$; $\epsilon_{294}=11940$;
(j) 5-[(R,S)-2-[[(R)-β-hydroxyphenethyl]amino]propyl]-2-thienyl methyl ketone; $[\alpha]_D^{20}=-23°$ (c=0.1% in methanol); UV: $\epsilon_{264}=8410$; $\epsilon_{294}=11260$;
(k) methyl 5-[(R,S)-3-[[(R)-β-hydroxyphenethyl]amino]butyl]-2-thiophenecarboxylate of melting point 102°–103°; $[\alpha]_D=-27°$ (c=0.1% in methanol); UV: $\epsilon_{255}=9500$; $\epsilon_{279}=12620$.

The ethyl (E)-5-[(R,S)-3-aminobutyl]-β-methyl-2-thiopheneacrylate used for the manufacture of the alcohols in sections (b) and (e) can be prepared as follows:

(R,S)-4-(2-thienyl)-2-butanol (Coll. Czech, Chem. Comm. 41, 1976, 479), acetyl chloride and aluminium chloride were reacted in methylene chloride to give (R,S)-3-(5-acetyl-2-thienyl)-1-methylpropyl acetate. This was saponified with sodium hydroxide in methanol to give (R,S)-5-(3-hydroxybutyl)-2-thienyl methyl ketone. This was reacted in alcohol with triethyl phosphonoacetate in the presence of sodium alcoholate to give ethyl (E)-5-[(R,S)-3-hydroxybutyl]-β-methyl-2-thiopheneacrylate. Reaction with p-toluenesulphochloride and subsequent treatment with sodium azide gave ethyl (E)-5-[(R,S)-3-azidobutyl]-β-methyl-2-thiopheneacrylate. Therefrom there was obtained by reduction with triphenylphosphine and subsequent hydrolysis ethyl (E)-5-[(R,S)-3-aminobutyl]-β-methyl-2-thiopheneacrylate; UV: $\epsilon_{320}=17465$.

The 5-(2-aminoethyl)-2-thiophenecarboxamide used for the preparation of the alcohol in section (c) can be prepared as follows:

2-(2-Thienyl)ethyl p-toluenesulphonate (J.A.C.S. 95, 1973, 1247), acetyl chloride and aluminium chloride were reacted in methylene chloride to give 2-[(5-acetyl-2-thienyl)ethyl]p-toluenesulphonate (melting point 111°–112°, from ethanol). This was converted with sodium azide in dimethyl sulphoxide into 5-(2-azidoethyl)-2-thienyl methyl ketone. Oxidation with sodium hypobromite yielded 5-(2-azidoethyl)-2-thiophenecarboxylic acid of melting point 53°–55° C. Treatment of this acid with thionyl chloride gave the corresponding acid chloride which was reacted with ammonia to give 5-(2-azidoethyl)-2-thiophenecarboxamide (melting point 104°–105°, from ethanol). Reaction of this amide with triphenylphosphine and hydrolysis (J. Org. Chem. 40, 1975, 1659) gave 5-(2-aminoethyl)-2-thiophenecarboxamide of melting point 134°–136° (from acetonitrile).

The 5-[(R,S)-2-aminopropyl]-2-thiophenecarboxamide used for the preparation of the alcohol in section (d) can be prepared as follows:

α-Methyl-2-thiopheneethanol (J.A.C.S. 64, 1942, 477), acetyl chloride and aluminium chloride were reacted in methylene chloride to give (R,S)-2-(5-acetyl-2-thienyl)-1-methylethyl acetate. This was saponified with sodium hydroxide in methanol to give 5-[(R,S)-2-hydroxypropyl]-2-thienyl methyl ketone which was subsequently reacted with p-toluenesulphochloride to give (R,S)-2-(5-acetyl-2-thienyl)-1-methylethyl p-toluenesulphonate of melting point 101°–103°. Therefrom there was obtained with sodium azide in dimethyl sulphoxide 5-[(R,S)-2-azidopropyl]-2-thienyl methyl ketone which was oxidized with bromine in sodium hydroxide to give 5-[(R,S)-2-azidopropyl]-2-thiophenecarboxylic acid. This acid was converted with thionyl chloride into the corresponding acid chloride from which there was obtained by treatment with ammonia 5-[(R,S)-2-azidopropyl)-2-thiophenecarboxamide of melting point 79°–80° (from ether). Treatment of this amide with triphenylphosphine and hydrolysis gave 5-[(R,S)-2-aminopropyl]-2-thiophenecarboxamide of melting point 91°–92° (from acetonitrile).

The ethyl (E)-5-[(R,S)-2-aminopropyl]-β-methyl-2-thiopheneacrylate used for the preparation of the alcohols in sections (g) and (h) can be prepared as follows:

5-[(R,S)-2-hydroxypropyl]-2-thienyl methyl ketone and triethyl phosphonoacetate were reacted in alcohol in the presence of sodium ethylate to give ethyl (E)-5-[(R,S)-2-hydroxypropyl]-β-methyl-2-thiopheneacrylate. With p-toluenesulphochloride there was obtained therefrom ethyl (E)-β-methyl-5-[(R,S)-2-[(p-toluenesulphonyl)oxy]propyl]-2-thiopheneacrylate (melting point 121°, from methylene chloride/alcohol). Reaction of this ester with sodium azide in dimethyl sulphoxide gave ethyl (E)-5-[(R,S)-2-azidopropyl]-β-methyl-2-thiopheneacrylate. Reduction of the latter ester with triphenylphosphine and hydrolysis led to ethyl (E)-5-[(R,S)-2-aminopropyl]-β-methyl-2-thiopheneacrylate; UV: $\epsilon_{320}=17970$.

The 2-acetyl-5-[(R,S)-3-aminobutyl]thiophene used for the preparation of the alcohol in section (i) can be prepared as follows:

(R,S)-5-(3-hydroxybutyl)-2-thienyl methyl ketone is reacted with p-toluenesulphochloride to give (R,S)-3-(5-acetyl-2-thienyl)-1-methylpropyl p-toluenesulphonate of melting point 61°-63°. Therefrom by treatment with sodium azide there is obtained methyl (R,S)-5-(3-azidobutyl)-2-thienyl ketone which is catalytically hydrogenated to give 2-acetyl-5-[(R,S)-3-aminobutyl]thiophene.

The 2-acetyl-5-[(R,S)-2-aminopropyl]thiophene used for the preparation of the alcohol in section (j) can be prepared by reacting 5-[(R,S)-2-azidopropyl]-2-thienyl methyl ketone with triphenylphosphine and subsequently hydrolyzing the product with aqueous ammonia.

The methyl 5-[(R,S)-3-aminobutyl]-2-thiophenecarboxylate used for the preparation of the alcohol in section (k) can be prepared by reacting methyl 5-(3-azidobutyl)-2-thiophenecarboxylate with triphenylphosphine in pyridine and hydrolyzing the product with concentrated ammonia to give methyl 5-[(R,S)-3-aminobutyl]-2-thiophenecarboxylate; UV: $\epsilon_{278}=11280$; $\epsilon_{254}=8760$.

EXAMPLE 38

In accordance with Example 1, from methyl p-[3-[[(R)-β-hydroxyphenethyl]amino]propyl]benzoate there was obtained methyl p-[3-[(S)-2-phenyl-1-aziridinyl]propyl]benzoate as an oil; UV: $\epsilon_{238}=17130$; $[\alpha]_D^{20}=+85°$ (c=0.8% in methanol).

EXAMPLE 39

In accordance with Example 1, from methyl p-[3-(S)-[[(R,S)-β-hydroxy-m-(trifluoromethyl)phenethyl]amino]butyl]-β-methylcinnamate there were obtained
methyl (E)-β-methyl-p-[(S)-3-[(R)-2-(α,α,α-trifluoro-m-tolyl)-1-aziridinyl]butyl]cinnamate as a colourless oil, $[\alpha]_D^{20}=-49°$ (c=0.5% in methanol), UV: $\epsilon_{274}=18250$, and
methyl (E)-β-methyl-p-[(S)-3-[(S)-2-(α,α,α-trifluoro-m-tolyl)-1-aziridinyl]butyl]cinnamate as a colourless oil, $[\alpha]_D^{20}=+100°$ (c=0.6% in methanol), UV: $\epsilon_{274}=19880$.

EXAMPLE 40

In accordance with Example 1, from methyl p-[3-(R)-[[(R,S)-β-hydroxy-m-(trifluoromethyl)phenethyl]amino]butyl]-β-methylcinnamate there were obtained
methyl (E)-β-methyl-p-[(R)-3-[(S)-2-(α,α,α-trifluoro-m-tolyl)-1-aziridinyl]butyl]cinnamate as a colourless oil, $[\alpha]_D^{20}=+53°$ (c=0.7% in methanol), UV: $\epsilon_{274}=19840$, and
methyl (E)-β-methyl-p-[(R)-3-[(R)-2-(α,α,α-trifluoro-m-tolyl)-1-aziridinyl]butyl]cinnamate as a colourless oil, $[\alpha]_D^{20}=-104°$ (c=1.0% in methanol); UV: $\epsilon_{274}=19040$.

EXAMPLE 41

In accordance with Example 1, from p-[(R)-3-[[(R,S)-β-hydroxy-m-(trifluoromethyl)phenethyl]amino]butyl]benzamide there was obtained p-[(R)-3-[2-(α,α,α-trifluoro-m-tolyl)-1-aziridinyl]butyl]benzamide in the form of an approximately 1:4 mixture of the 2-R form and the 2-S form; melting point 149°-153° (from ether); $[\alpha]_D^{20}=+49°$ (c=0.7% in methanol); UV: $\epsilon_{230}=17820$.

EXAMPLE 42

Tablets having the following composition are manufactured in the usual manner:

| | |
|---|---|
| Active substance of formula I or II-1, e.g. p-[(S)—3-[(S)—2-phenyl-1-aziridinyl]butyl]benzamide dihydrochloride | 250 mg |
| Lactose | 200 mg |
| Corn starch | 300 mg |
| Corn starch paste | 50 mg |
| Calcium stearate | 5 mg |
| Dicalcium phosphate | 45 mg |

We claim:
1. Compounds of the formula

$$Z^1-\underset{\underset{OH}{|}}{CH}-CH_2-NH-\underset{\underset{R^2}{|}}{\overset{\overset{R^1}{|}}{C}}-(CH_2)_n-Z^{21} \qquad \text{II-1}$$

wherein $Z^1$ is a group of the formula

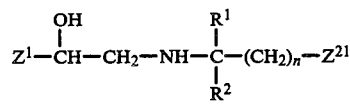

$Z^{21}$ is a group of the formula

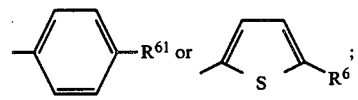

$R^1$ and $R^2$ are hydrogen or lower-alkyl; $R^3$ is hydrogen, halogen, hydroxy, benzyloxy, lower-alkyl, lower-alkoxy, hydroxymethyl, amino, acylamino, lower-alkoxybenzylamino, nitro, carbamoyl, trifluoromethyl or lower-alkylsulphonylmethyl; $R^4$ and $R^5$ are hydrogen, halogen or hydroxy; $R^6$ is lower-alkanoyl, carboxy, cyano, hydroxy, hydroxy-lower-alkyl, acyloxy or a group $-C(R^7)=C(R^8)COOR^9$, $-SO_2R^{10}$, $-CH_2R^{10}$ or $-C(O)R^{10}$; $R^7$, $R^8$ and $R^9$ are hydrogen or lower-alkyl; $R^{10}$ is amino, mono- or di-lower-alkylamino, piperidino, morpholino, thiamorpholino, piperazino or the ether group of a lower aliphatic, cycloaliphatic or araliphatic alcohol or of a phenol; $R^{61}$ is a group $-CH_2R^{11}$ or $-SO_2R^{10}$; $R^{11}$ is piperidino, morpholino, thiamorpholino or piperazino; and, n is a whole number of 1-4; or physiologically compatible salts thereof.

2. Compounds according to claim 1 wherein $R^1$ is hydrogen and $R^2$ is hydrogen or methyl.

3. Compounds according to claim 2 wherein $R^2$ is methyl.

4. Compounds according to claim 1 wherein $R^3$ is hydrogen, halogen, lower-alkyl, lower-alkoxy or trifluoromethyl, $R^4$ is hydrogen or halogen and $R^5$ is hydrogen.

5. Compounds according to claim 1 wherein $R^3$ is hydrogen, chlorine or trifluoromethyl and $R^4$ and $R^5$ are hydrogen.

6. Compounds according to claim 5 wherein $R^3$ is in the meta-position.

7. Compounds according to claim 1 wherein $Z^{21}$ is a group of the formula

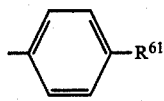

and wherein $R^{61}$ is sulphamoyl.

8. Compounds according to claim 1 wherein $Z^{21}$ is a group of the formula

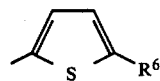

and $R^6$ is a group $-CH_2R^{10}$, $-C(O)R^{10}$, $-SO_2R^{10}$ or $-C(R^7)=C(R^8)COOR^9$.

9. Compounds according to claim 8 wherein $R^6$ is a group $-C(O)R^{10}$ or $-C(R^7)=C(R^8)COOR^9$ and wherein $R^7$ and $R^9$ are lower alkyl and $R^8$ is hydrogen.

10. Compounds according to claim 8 wherein $R^6$ is carbamoyl or 2-ethoxycarbonyl-1-methylvinyl.

11. A compound in accordance with claim 1, p-[3-[[(R)-betahydroxyphenethyl]amino]propyl]benzenesulphonamide or a physiologically compatible salt thereof.

12. A compound in accordance with claim 1, p-[(S)-3-[[(R)beta-hydroxyphenethyl]amino]butyl]benzenesulphonamide or a physiologically compatible salt thereof.

13. A compound in accordance with claim 1, p-[(R)-3-[[[(R)beta-hydroxyphenethyl]-amino]-3-methylpropyl]benzenesulphonamide or a physiologically compatible salt thereof.

* * * * *